US012575751B2

(12) United States Patent
Chang

(10) Patent No.: US 12,575,751 B2
(45) Date of Patent: Mar. 17, 2026

(54) PORTABLE HEART MONITOR

(71) Applicant: Kuo-Yuan Chang, New Taipei (TW)

(72) Inventor: Kuo-Yuan Chang, New Taipei (TW)

( * ) Notice: Subject to any disclaimer, the term of this patent is extended or adjusted under 35 U.S.C. 154(b) by 576 days.

(21) Appl. No.: 18/090,032

(22) Filed: Dec. 28, 2022

(65) Prior Publication Data

US 2024/0148263 A1 May 9, 2024

(30) Foreign Application Priority Data

Nov. 9, 2022 (TW) .................................. 111142754

(51) Int. Cl.
| | |
|---|---|
| *A61B 5/024* | (2006.01) |
| *A61B 5/00* | (2006.01) |
| *A61B 5/0205* | (2006.01) |
| *A61B 5/026* | (2006.01) |
| *A61B 5/1455* | (2006.01) |
| *A61B 5/08* | (2006.01) |

(52) U.S. Cl.
CPC ........ *A61B 5/02438* (2013.01); *A61B 5/0205* (2013.01); *A61B 5/0261* (2013.01); *A61B 5/14551* (2013.01); *A61B 5/72* (2013.01); *A61B 5/0816* (2013.01); *A61B 2560/0431* (2013.01)

(58) Field of Classification Search
CPC .............. A61B 5/0205; A61B 5/02416; A61B 5/02438; A61B 5/02; A61B 5/02427;

A61B 5/0261; A61B 5/1455; A61B 5/14551; A61B 5/14552; A61B 5/14542; A61B 5/6802; A61B 5/6826; A61B 5/72
See application file for complete search history.

(56) References Cited

U.S. PATENT DOCUMENTS

| | | | | |
|---|---|---|---|---|
| 2008/0221418 A1* | 9/2008 | Al-Ali | ................ | A61B 5/02416 |
| | | | | 600/324 |
| 2015/0164339 A1* | 6/2015 | Xu | ..................... | A61B 5/02416 |
| | | | | 600/324 |
| 2019/0350470 A1* | 11/2019 | Khachaturian | .... | A61B 5/02055 |
| 2023/0172499 A1* | 6/2023 | Marriott | ............. | A61B 5/14552 |
| | | | | 600/323 |

FOREIGN PATENT DOCUMENTS

| | | |
|---|---|---|
| CN | 201033073 Y | 3/2008 |
| TW | 201325553 A | 7/2013 |
| TW | I619472 B | 4/2018 |

* cited by examiner

*Primary Examiner* — Chu Chuan Liu
(74) *Attorney, Agent, or Firm* — Muncy, Geissler, Olds & Lowe, P.C.

(57) ABSTRACT

A portable heart monitor includes a detecting unit to output a detecting light beam and receive a physiological response signal, wherein the physiological response signal is generated by the reaction of the detecting light beam and a finger of a user. The physiological response signal includes pulse waves of a perfusion index (PI). A processing and analyzing unit processes and analyzes the physiological response signal to acquire an analysis result, which is to be shown on a prompting unit. The analysis result includes heart status information based on processing of the pulse signals of the perfusion index (PI).

11 Claims, 3 Drawing Sheets

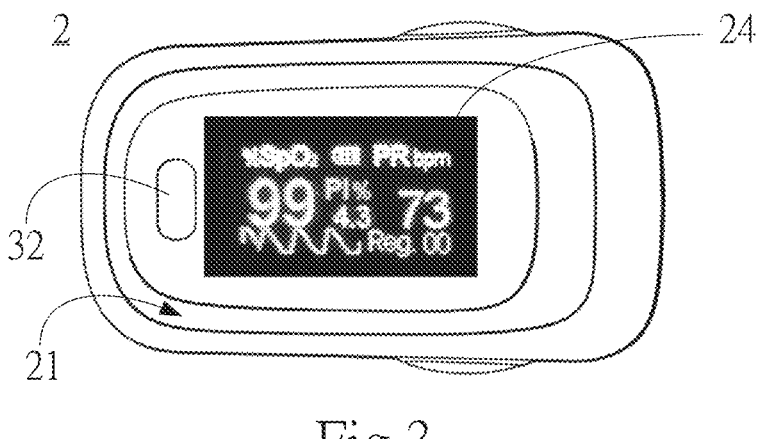
Fig.3
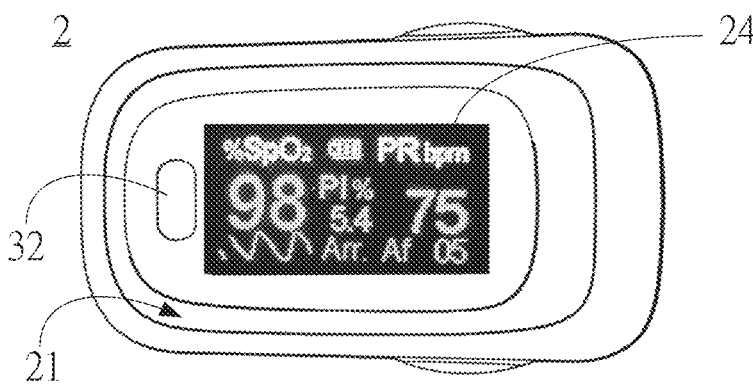
Fig.4
Fig.5

PORTABLE HEART MONITOR

CROSS REFERENCES

This application claims benefit of TW Patent Application No. 111142754 filed on 2022 Nov. 9 and titled as "PORTABLE HEART MONITOR", the disclosure of which is hereby incorporated by references.

1. FIELD OF THE INVENTION

The present invention relates to a heart monitor, particularly to a portable heart monitor able to warn the user of possibilities for arrhythmia or atrial fibrillation.

2. DESCRIPTION OF THE PRIOR ART

Homecare is getting popular now. The oximeter is an indispensable device for home care. It is a tendency to miniaturizing the oximeter into a small appliance that is portable and able to instantly provide blood oxygen information. Even hospitals usually adopt fingertip oximeter to measure blood oxygen and heartbeat nowadays. However, the conventional fingertip oximeter does not have additional functions to detect the status and performance of hearts.

About the functions of monitoring hearts, a Taiwan patent of publication No. 201325553 disclosed a blood oxygen measurement system able to detect and display the information of arrhythmia, which uses the frequency variation of the pulse signals of blood oxygen to work out the information of arrhythmia. Atrial fibrillation (Af) is a commonly-seen disease of arrhythmia. A Taiwan patent of No. 1619472 disclosed a method and device for detecting atrial fibrillation, which converts a sphygmogram into an energy spectrogram and counts the number of spikes to determine whether atrial fibrillation occurs. A China utility model patent of No. CN201033073Y disclosed a pulse rate and blood oxygen measurement device, which can measure blood oxygen saturation level (SpO2), pulse rates (PR), and perfusion indexes (PI).

The perfusion index reflects the state of pulsatile blood flow, i.e. the capability of blood perfusion. The greater the pulsatile blood flow, the larger the pulsation, and the higher the PI value. The PI value is influenced by the measured area (such as skin, nail, or bone) and the blood perfusion state of the patient (the flow state of arterial blood). The sympathetic nerves influence heartbeat and arterial blood pressure (also influence pulses and arterial blood flow). Therefore, the neural regulation system and the metal state would indirectly influence the PI value. In clinics, the PI value is used to determine the effect and extent of anesthesia and whether the sympathetic chains is cut off successfully and completely.

SUMMARY OF THE INVENTION

A portable heart monitor is provided to be an AI heartbeat rate analyzer convenient to be carried about. A user may measure blood oxygen easily and learn the possibilities of some heart issues at same time by persistently performing measurement for a given interval of time to acquire the perfusion index (PI) of the finger. The heart issues herein are such as premature ventricular contraction, atrial fibrillation, too fast/too slow a heartbeat, arrhythmia, cardiac murmur, etc. With the messages provided by the portable heart monitor, the user may look for professional diagnosis and therapy earlier.

Herein is provided a portable heart monitor, which exempts the user from persistently wearing the monitoring device for a long period of time to acquire the data for analyzing the state of his heart, and which uses artificial intelligence (AI) to analyze the PI signals from the user's finger to determine whether the user's heart beats regularly, suffers atrial fibrillation, or has arrhythmia.

In one embodiment, the portable heart monitor of the present invention comprises a detecting unit outputting a detecting light beam and receiving a physiological response signal, wherein the physiological response signal results from the reaction of the detecting light beam and a finger of the user and includes pulse signals of a perfusion index; a processing and analyzing unit receiving the physiological response signal from the detecting unit and calculating and analyzing the physiological response signal to output an analysis result, wherein the analysis result includes heart status information obtained by calculating the PI pulse signals of the perfusion index; a prompting unit receiving and presenting the analysis result coming from the processing and analyzing unit; and a power supply unit connected with and supplying power to the detecting unit, the processing and analyzing unit, and the prompting unit.

BRIEF DESCRIPTION OF THE DRAWINGS

FIG. 3 schematically shows a top view of a portable heart monitor according to one embodiment of the present invention.

FIG. 4 schematically shows another top view of a portable heart monitor according to one embodiment of the present invention.

FIG. 5 schematically shows yet another top view of a portable heart monitor according to one embodiment of the present invention.

DESCRIPTION OF THE PREFERRED EMBODIMENT

Figure 1:
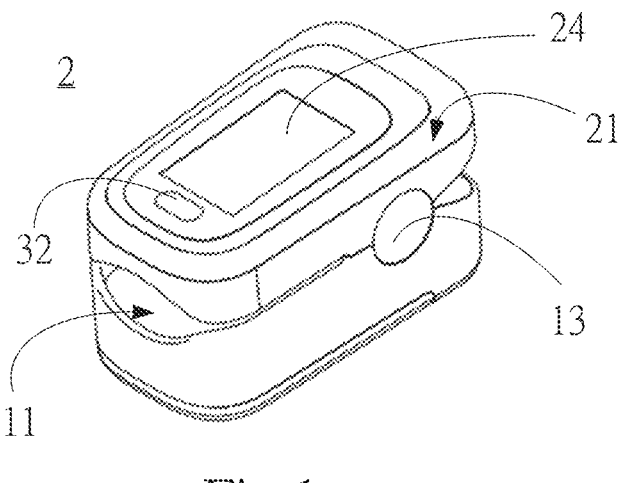
FIG. 1 is a perspective view schematically showing an appearance of a portable heart monitor according to a first embodiment of the present invention.

Refer to FIG. 1 FIG. 1 is a perspective view schematically showing an appearance of a portable heart monitor according to a first embodiment of the present invention. The portable heart monitor 2 includes a housing 21 and other units for detection, calculation, analysis and display are encapsulated by or disposed on the housing 21. For example, a display screen 24 and a power button 32 are disposed on the housing 21, and an opening 11 is formed on the sidewall of the housing 21. In the embodiment, the portable heart monitor 2 is a portable fingertip heart monitor, and the opening 11 provides an accommodation space allowing a user's finger to be placed into and secured inside the portable heart monitor 2 for detection. It is easily understood: the portable heart monitor 2 also have another design or mechanism to convenience the usage of users. For example, a control mechanism 13 is an elastic pivot able to control the size of the opening 11, whereby the user's finger may be inserted into the accommodation space and secured thereinside conveniently. The power button 32 may be used to turn on the power of the portable heart monitor 2 or further include switching the presenting way of the information shown on the display screen 24. For example, after measurement, the user switches to convert the information presented horizontally into the information presented vertically. In the embodiment, once the portable heart monitor 2 detects the sensed region of the user, such as a portion of the finger placed in sensing position (not shown in the drawing) inside the opening 11, the portable heart monitor 2 may perform measurement automatically without user's starting operation. After measurement, the portable heart monitor 2 presents the analysis result on the display screen 24. If the user has not undertaken any operation for a given interval of time or the finger has left the sensing position for a given interval of time, the portable heart monitor 2 automatically turns off the power. Such an operation and detection way greatly simplifies the usage for the user and maximizes the power efficiency. It is unnecessary for the portable heart monitor 2 to mechanically or electrically connect with external devices. The user may carry about the portable heart monitor 2 constantly to timely perform measurement and instantly learn the measurement results. It is mainly the user's finger that is used as the sensed region to contact the portable heart monitor 2. For example, a finger sleeve, a soft ring, or a hard ring, which surrounds the finger belly, or another device, may be used to contact the finger for measurement. However, the present invention is neither limited by FIG. 1 nor limited by the above statement. Any modified design, which can implement the operation of the portable heart monitor 2, is to be also included by the scope of the present invention.

Figure 2:
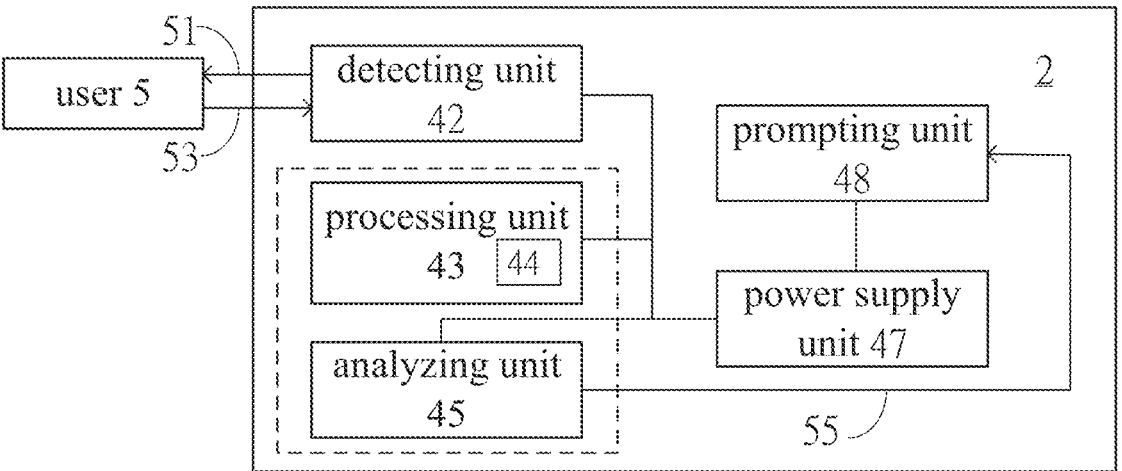
FIG. 2 is a block diagram schematically showing the system of the portable heart monitor according to the first embodiment of the present invention.

FIG. 2 is a block diagram schematically showing the system of the portable heart monitor according to the first embodiment of the present invention. Referring to FIG. 1 and FIG. 2, the portable heart monitor 2 includes a detecting unit 42, a processing unit 43, an analyzing unit 45, a prompting unit 48, and a power supply unit 47. Each of the abovementioned units may include one or more modules/mechanisms/elements to be disposed inside or on the housing of the portable heart monitor 2. The power supply unit 47 are electrically connected with and supplies power to the detecting unit 42, the processing unit 43, the analyzing unit 45 and the prompting unit 48 respectively. In practice, the power supply unit 47 may be a primary battery or a secondary battery. If the power supply unit 47 is a secondary battery, the power supply unit 47 may further include circuits and mechanisms for charging the secondary battery.

Refer to FIG. 1 and FIG. 2 again. The detecting unit 42 includes a physiological signal interface to output a detecting light beam 51 acting on the user 5. A physiological response signal 53 is sent back to the portable heart monitor 2 for processing through the physiological signal interface. The physiological signal interface may be disposed in the accommodation space of the opening 11. The detecting light beam 51 is projected to the sensing position to act on the sensed region of the user 5 and then form the physiological response signal 53 that is sent back through the physiological signal interface. In the embodiment, the detecting light beam 51 is a light signal of an infrared signal or a far-infrared signal. The physiological response signal 53 may include the pulse signal of blood oxygen, the pulse signal of heartbeat or the pulse signal of the perfusion index, which is received within a given interval of time, such as 15-30 seconds. Next, the detecting unit 42 transmits the measured physiological response signal 53 to the processing unit 43 for pre-processing such as filtering, de-noising, and amplifying the signal-to-noise ratio, and then transmits the pulse signals to the analyzing unit 45. The analyzing unit 45 may utilize artificial intelligence to calculate and analyze the pulse signals with the Fast-Fourier Transformation (FFT). For example, the continuous PI signals and PI fluctuation of blood oxygen are continuously calculated to acquire the related parameters such as heartbeats, pulse rate values and the blood oxygen values as the measurement results.

Refer to FIG. 1 and FIG. 2 again. The portable heart monitor 2 of the present invention operates with artificial intelligence that the computer program processes massive data of a PI waveform database, persistently analyzes and modifies the data, and cooperates with the heart-spectrum algorithm to generate the AI analyzed data of the present invention. The analyzing unit 45 of the present invention calculates the physiological signals obtained in continuous measurement, analyzes and modifies the data acquired from the physiological signals, and then interprets the corresponding data to obtain the measurement results. The present invention is characterized in that the analyzing unit 45 performs at least one of a frequency-domain transformation and a time-domain transformation of the pulse signals of PI to acquire the PI values and the result of analyzing the heart state by comparing the differential and difference of the PI fluctuation in the time domain and in the frequency domain. Different from measuring pressure acting on a vessel for a typical blood pressure measurement, the perfusion index (PI) measurement is to measure the extent of the vessel expansion in the area the blood flows through. In the present invention, through the analysis of the pulse signal of the perfusion index in the finger, an analyzing result may learn the possibilities of at least two of the following phenomena: premature ventricular contraction, atrial fibrillation, too fast/too slow a heartbeat, arrhythmia, and cardiac murmur.

Refer to FIG. 1 and FIG. 2 again. Then, the analyzing unit 45 transmits measuring and analyzing results 55 to the prompting unit 48 to make the user know them. For example, the display screen is used to display a portion or all of the measuring results to the user, such as at least two of a respiration rate, a blood oxygen value, a heartbeat rate, a perfusion index and a perfusion waveform. It should be noted: while the detecting unit 42 outputs a detecting light beam 51 to act on the user 5, the prompting unit 48 may simultaneously present dynamic information to the user 5 to remind the user 5 that the measurement is being undertaken. In one embodiment, the processing unit 43 and the analyzing unit 45 may be integrated into a processing and analyzing unit. For example, the processing and analyzing unit may be realized with a single chip, a plurality of chips, or a combination of a computation processor, a memory and circuits. Furthermore, the prompting unit 48 may present the measurement results and the analysis results in form of numbers, figures, and/or text. One of the characteristics of the present invention is that the prompting information includes the heart status information, such as regular heartbeat, atrial fibrillation and/or arrhythmia, which is obtained via analyzing the pulse signals of the perfusion index and determined with AI.

Refer to FIG. 1 and FIG. 2 again. In one embodiment, the processing unit 43 further includes an Auto Gain Control (AGC) block 44 to perform the AGC function. The portable heart monitor of the present invention acquires the analysis results via measuring the pulse signals of the perfusion index of the finger. However, the fingers are the distal extremities of a human body (or a primate body) and frequently exposed to the external environment. While a finger is exposed to the external environment in much lower temperature than human body for a long time, the PI value of the finger will be reduced. In such a case, the cold finger would degrade the quality of the pulse signals of the perfusion index. Thus, once recognizing such pulse signals in poor quality, the processing unit 43 of the present invention may utilize the AGC block 44 with the AGC function to enhance the effective portions of the physiological response signals 53. In detail, the physiological response signal 53 (the light transmitting signal) is converted into electrical signals including DC signals and AC signals. The AC signals represent the voltages of the pulses, and the PI values are proportional to the AC signals. The AGC function of the AGC block 44 may increase the effective digits of the AC signals and enhance the ability of analyzing the PI values. Thus, even though the user has a weak perfusion in measurement, the present invention can still perform analysis to acquire the physiological response signal 53 that represents the pulses of the heart. Optionally, the processing unit 43 may call the AGC block 44 to control the detecting unit 42 to adjust the detecting light beam 51 for the required intensity, whereby the present invention can still detect the heartbeat while the user has a weak perfusion.

Refer to FIGS. 3, 4 and 5, which are top views of a portable heart monitor according to one embodiment of the present invention. The housing 21 of the portable heart monitor 2 of the present invention has a display screen 24 and a power button 32. The user may operate the power button 32 to turn on the display screen 24 to display ready for measurement. In one embodiment, while the measurement has not been started yet, the display screen 24 presents the names of the items. The items may be but is not limited to be respiration rate, "% SpO2" (the concentration of blood oxygen), "PR bpm" (pulse rate), and state of charge. After measurement, the display screen 24 further presents the values of the items and other analysis results, such as "PI %" (the perfusion index). As shown in FIG. 3, after measurement, the concentration of blood oxygen is 99; the PI value is 4.3; the pulse rate is 73. Besides, the display screen 24 may further present the waveform obtained via analyzing the measured PI values and even the interpretation of the waveform, such as "Reg.00", wherein 00 expresses the frequency; "Reg00" indicates that the presented waveform is determined to be normal. It is understood herein: the arrangement of the information presented on the display screen 24, including item names, figures, units, values and waveforms, is not limited shown in FIGS. 3-5. Any other arrangements, which are the modifications of FIGS. 3-5, may be used in the present invention as long as the arrangements favor users to understand the measurement results.

Refer to FIG. 4. FIG. 4 shows measurement results different from the measurement results shown in FIG. 3. In FIG. 4, the concentration of blood oxygen is 98; the PI value is 8.2; the pulse rate is 73; the interpretation of the waveform obtained via analyzing the measured PI values is presented as "Arr.02". The message of "Arr.02" indicates that the user may suffer arrhythmia and has two frequencies (heart noises) that should not appear. Refer to FIG. 5. In FIG. 5, the concentration of blood oxygen is 98; the PI value is 5.4; the pulse rate is 75; the interpretation of the waveform obtained via analyzing the measured PI values is presented as "Arr. Af 05". The message of "Arr. Af 05" indicates that the user may suffer arrhythmia and atrial fibrillation and has five frequencies (heart noises) that should not appear. Therefore, the portable heart monitor of the present invention may be carried about by the user and execute measurement any time when the user would like to monitor the heart of the user, present the measurement and analysis results in a simple and clear way without complicated setting or installation. Thereby, the user can learn the possible risks of his heart instantly and deal with the problems early.

Refer to Table.1. The outputs of analyzing the result of a conventional 12-lead electrocardiography are used as a reference group and compared with the outputs of analyzing the result of the portable heart monitor of the present invention. It is found: the outputs of the portable heart monitor are consistent with the outputs of the conventional electrocardiographic device. In comparison with the conventional electrocardiographic devices, the portable heart monitor of the present invention is lightweight, power-efficient, portable, able to perform measurement anytime, able to output measurement results instantly, able to output measurement results consistent with the measurement results of the conventional electrocardiographic device, and free from persistent measurement. Thereby, the user may take the succeeding actions as soon as possible; for example, the user may seek for medical care early.

TABLE 1

| Gender M: male F: female | Age | Measurement results of 12-lead ECG 1: having Af 0: free of Af | Heart rhythm measured by the AI-based heart monitor of the present invention 1: arrhythmic 0: rhythmic | Heart state detected by the AI-based heart monitor of the present invention 1: Af, atrial fibrillation 2: Arrh, arrhythmia 0: free of Af/Arrh |
|---|---|---|---|---|
| M | 52 | 1 | 1 | 1 |
| M | 75 | 1 | 1 | 1 |
| F | 87 | 0 | 0 | 0 |
| M | 73 | 1 | 1 | 1 |
| m | 59 | 0 | 0 | 0 |
| F | 89 | 1 | 1 | 1 |
| M | 65 | 0 | 0 | 0 |
| M | 97 | 1 | 1 | 1 |
| F | 75 | 1 | 1 | 1 |
| F | 89 | 1 | 1 | 1 |
| F | 79 | 1 | 1 | 1 |
| F | 69 | 0 | 0 | 0 |
| M | 88 | 1 | 1 | 1 |
| M | 90 | 1 | 1 | 1 |
| F | 89 | 1 | 1 | 0 |
| F | 68 | 1 | 1 | 1 |
| F | 69 | 1 | 1 | 1 |
| F | 73 | 1 | 1 | 1 |
| F | 67 | 1 | 1 | 1 |
| M | 71 | 0 | 0 | 0 |
| M | 47 | 1 | 1 | 0 |
| M | 49 | 0 | 0 | 0 |
| M | 59 | 0 | 0 | 0 |
| M | 90 | 1 | 1 | 1 |
| M | 61 | 0 | 0 | 0 |
| M | 92 | 1 | 1 | 1 |
| M | 79 | 0 | 0 | 0 |
| F | 95 | 0 | 0 | 0 |
| F | 80 | 1 | 1 | 1 |
| F | 75 | 1 | 1 | 1 |
| M | 88 | 1 | 1 | 1 |
| F | 88 | 1 | 1 | 1 |
| M | 95 | 1 | 1 | 1 |
| M | 87 | 0 | 0 | 0 |
| F | 99 | 0 | 0 | 0 |
| M | 85 | 0 | 0 | 0 |

Figure 6:
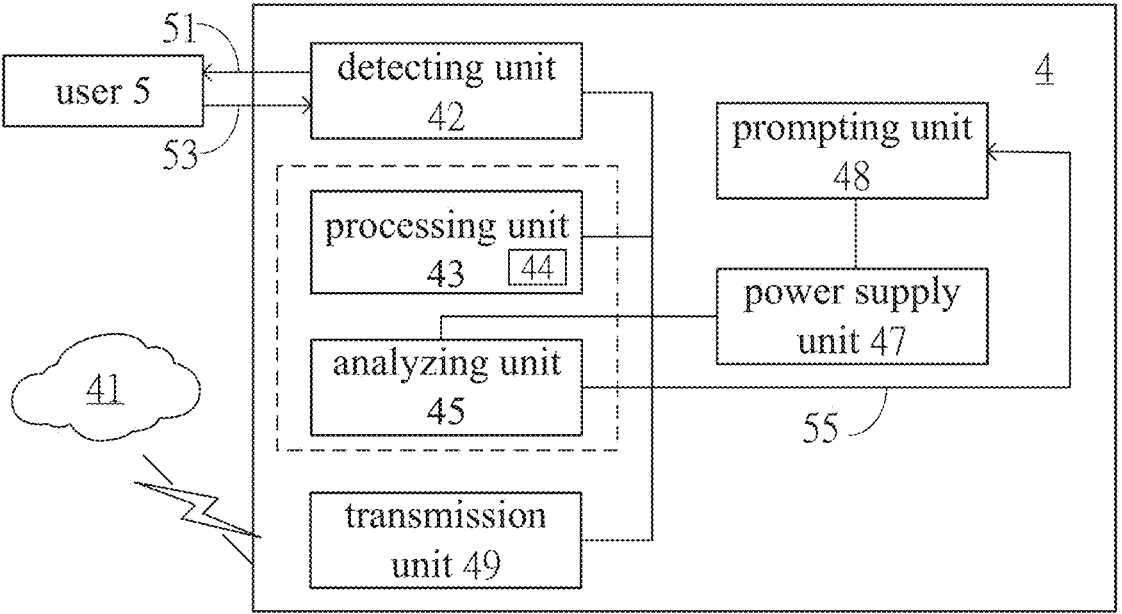
FIG. 6 is a block diagram schematically showing the system of the portable heart monitor according to a second embodiment of the present invention.

Refer to FIG. 6. FIG. 6 is a block diagram schematically showing the system of the portable heart monitor according to a second embodiment of the present invention. The portable heart monitor 4 includes a detecting unit 42, a processing unit 43, an analyzing unit 45, a prompting unit 48, a power supply unit 47, and a transmission unit 49. The detecting unit 42, the processing unit 43, the analyzing unit 45, the prompting unit 48, and the power supply unit 47 of the portable heart monitor 4 are similar to those of the portable heart monitor 2 and will not repeat herein. After the analyzing unit 45 performs a preliminary analysis of the pulse signals, a portion of the data obtained in the preliminary analysis may be wirelessly sent out through the transmission unit 49 to a cloud 41 for storage, computation, analysis and feedback. The transmission unit 49 includes wireless transmission functions, such as Bluetooth, WiFi, and/or General Packet Radio Service (GPRS). The cloud 41 includes servers and databases, wherein the AI technology may be used to perform more accurate analysis on the data continuously to obtain the measurement results, and then the results are stored in the cloud 41. Therefore, while the individual pieces of data and measurement results are stored in the cloud 41, the AI technology may be used to acquire the continuous measurement results more completely. Then, the measurement results are sent back to the portable heart monitor 4 to prompt the user 5 through the prompting unit 48, which may use warning lights, text, sounds or voices to prompt the user 5.

In conclusion, the portable heart monitor of the present invention exempts the user from the conventional problem that the data for analyzing the status of the heart cannot be obtained unless the user wears the monitoring device for a period of time. The portable heart monitor of the present invention reminds users of the possibilities of some heart problems through analyzing the PI signals. The user may perform measurements anytime and learn the results instantly. Thereby, the user may take succeeding actions as early as possible. Furthermore, the functions of measurement, analysis and display are jointly integrated into the portable heart monitor of the present invention. The user needn't upload data to a cloud or connect the portable heart monitor with an external device. The persons who are unfamiliar with installing and using APP software of mobile phones can still operate the present invention independently. Therefore, the present invention is user-friendly and enables users to perform measurements by themselves.

The embodiments described above are to demonstrate the technical thoughts and characteristics of the present invention to enable the persons skilled in the art to understand, make, and use the present invention. However, it should be understood: these embodiments are only to exemplify the present invention but not to limit the scope of the present invention. Therefore, any equivalent modification or variation according to the spirit of the present invention is to be also included by the scope of the present invention.

What is claimed is:

1. A portable heart monitor, comprising a detecting unit that comprises a physiological signal interface for outputting a detecting light beam and receiving a physiological response signal, wherein the physiological response signal is generated in response to the detecting light beam's action on a finger of a user, and the physiological response signal includes pulses of a perfusion index (PI);
a processing and analyzing unit that, receiving the physiological response signal from the detecting unit, and calculating and analyzing the physiological response signal to output a measurement result and generate an analysis result using the measurement result, wherein the analysis result includes heart status information obtained by calculating the pulses of the perfusion index, wherein the heart status information includes a possibility of premature ventricular contraction, atrial fibrillation, arrhythmia or cardiac murmur, or possibilities of at least two of abovementioned;
a prompting unit, receiving and presenting the analysis result coming from the processing and analyzing unit; and
a power supply unit, connected with the detecting unit, the processing and analyzing unit and the prompting unit, and supplying power to the detecting unit, the processing and analyzing unit, and the prompting unit.

2. The portable heart monitor according to claim 1, wherein the processing and analyzing unit performs a frequency-domain transformation of the physiological response signal, a time-domain transformation of the physiological response signal, or both abovementioned.

3. The portable heart monitor according to claim 2, wherein the measurement result includes one or at least two of a respiration rate, a blood oxygen value, a heartbeat rate, a perfusion index, and a perfusion waveform or at least two of abovementioned.

4. The portable heart monitor according to claim 3, wherein the prompting unit includes a function of presenting the measurement result.

5. The portable heart monitor according to claim 1, wherein the prompting unit includes a function of presenting a respiration rate of the user.

6. The portable heart monitor according to claim 1, further comprising a housing accommodating the detecting unit, the processing and analyzing unit, the prompting unit and the power supply unit.

7. The portable heart monitor according to claim 1, wherein the prompting unit uses warning lights, text, sounds or voices to prompt the user.

8. The portable heart monitor according to claim 1, further comprising a transmission unit electrically connected with the processing and analyzing unit and the power supply unit, wherein the transmission unit transmits the physiological response signal to an external cloud for analysis.

9. The portable heart monitor according to claim 8, wherein the transmission unit transmits the physiological response signal to an external cloud in one or a least two of a Bluetooth technology, a WiFi technology, and a General Packet Radio Service (GPRS) technology.

10. The portable heart monitor according to claim 8, wherein the external cloud includes a cloud database for storing the physiological response signal.

11. The portable heart monitor according to claim 1, further comprising an Auto Gain Control (AGC) block, wherein the AGC block performs an AGC processing to the physiological response signal.

* * * * *